United States Patent
Sato et al.

(10) Patent No.: US 11,261,194 B2
(45) Date of Patent: *Mar. 1, 2022

(54) PRODUCTION METHOD OF DIOL

(71) Applicant: MITSUBISHI GAS CHEMICAL COMPANY, INC., Chiyoda-ku (JP)

(72) Inventors: Hideyuki Sato, Niigata (JP); Ryuji Hasemi, Niigata (JP)

(73) Assignee: MITSUBISHI GAS CHEMICAL COMPANY, INC., Chiyoda-ku (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/771,778

(22) PCT Filed: Dec. 6, 2018

(86) PCT No.: PCT/JP2018/044978
§ 371 (c)(1),
(2) Date: Jun. 11, 2020

(87) PCT Pub. No.: WO2019/117019
PCT Pub. Date: Jun. 20, 2019

(65) Prior Publication Data
US 2021/0188864 A1  Jun. 24, 2021

(30) Foreign Application Priority Data
Dec. 15, 2017 (JP) ............... JP2017-240303

(51) Int. Cl.
C07D 493/10 (2006.01)
(52) U.S. Cl.
CPC .................. C07D 493/10 (2013.01)
(58) Field of Classification Search
CPC .................................................. C07D 493/10
See application file for complete search history.

(56) References Cited

U.S. PATENT DOCUMENTS

| 3,708,502 A * | 1/1973 | Dunlop ............. C07D 317/20 549/370 |
| 10,633,391 B2 * | 4/2020 | Sato ................ C07D 493/10 |
| 2006/0057494 A1 | 3/2006 | Lee et al. |
| 2007/0129554 A1 | 6/2007 | Harrington et al. |
| 2015/0218117 A1 | 8/2015 | Yamashita et al. |
| 2017/0240495 A1 | 8/2017 | Okamoto et al. |
| 2019/0256524 A1 | 8/2019 | Sato et al. |

FOREIGN PATENT DOCUMENTS

| EP | 3 202 757 A1 | 8/2017 |
| JP | 59-148776 A | 8/1984 |
| JP | 2000-44570 A | 2/2000 |
| JP | 2005-29563 A | 2/2005 |
| JP | 2006-83172 A | 3/2006 |
| JP | 2008-297327 A | 12/2008 |
| JP | 2009-512724 A | 3/2009 |
| WO | WO-2007048717 A1 * | 5/2007 ........... C07D 241/20 |
| WO | WO 2016/052476 A1 | 4/2016 |
| WO | WO 2018/074305 A1 | 4/2018 |

OTHER PUBLICATIONS

Harper, Robert John Jr., "Kinetic and Equilibrium Studies of Cyclic Ketal Formation and Hydrolysis" Dissertation 1957, The Ohio State University.*
International Preliminary Report on Patentability and Written Opinion dated Jun. 16, 2020 in PCT/JP2018/044978 (with English Translation), citing documents AQ-AU therein, 11 pages.
Extended European Search Report dated Oct. 15, 2020 in corresponding European Patent Application No. 18888994.3, citing documents AA, AO and AX therein, 7 pages.
Roger W. Alder et al., "Attempted equilibration of an insoluble spiran polymer with monomers and oligomers through reversible chemical reactions: transketalization route to spiropolymers from 1,4-cyclohexanedione and pentaerythritol", Polymer, vol. 35, No. 26, XP055734344, 1994, pp. 5765-5772.

* cited by examiner

Primary Examiner — David K O'Dell
(74) Attorney, Agent, or Firm — Oblon, McClelland, Maier & Neustadt, L.L.P.

(57) ABSTRACT

Provided is a method for producing a diol represented by Formula (1), the method including using water as a solvent to carry out a cyclodehydration reaction of a 1,4-cyclohexanedione derivative represented by Formula (2) with a triol represented by Formula (3) to produce a diol represented by Formula (1). In Formula (1), $R^1$ and $R^2$ each independently denote a hydrocarbon group, and $R^3$ each independently denotes a hydrogen atom, a heteroatom-containing group, a halogen atom-containing group, a linear alkyl group having from 1 to 6 carbon atoms, a branched alkyl group having from 3 to 6 carbon atoms, or a group including an aryl group and having from 6 to 12 carbon atoms.

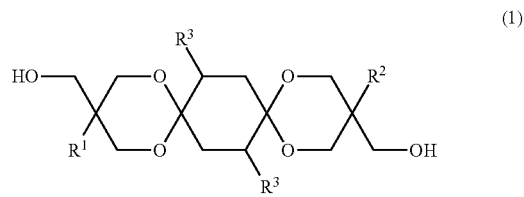

(1)

12 Claims, No Drawings

PRODUCTION METHOD OF DIOL

TECHNICAL FIELD

The present invention relates to a method for producing a diol having a dispiro structure.

BACKGROUND ART

Spiroglycol (3,9-bis(2-hydroxy-1,1-dimethyl ethyl)-2,4,8,10-tetraoxaspiro[5,5]undecane) has been studied in the past. For example, Patent Documents 1 to 3 disclose methods for producing polyhydric alcohols having a cyclic acetal such as spiroglycol, which is for producing polyhydric alcohols having a high purity cyclic acetal.

CITATION LIST

Patent Documents

Patent Document 1: JP 59-148776 A
Patent Document 2: JP 2000-44570 A
Patent Document 3: JP 2005-29563 A

SUMMARY OF INVENTION

Technical Problem

The spiroglycols described in Patent Documents 1 to 3 described above are excellent materials, but in recent years, even higher thermal stability has been demanded. Therefore, the present inventors discovered, as a novel diol having even higher thermal stability, a diol represented by Formula (1) described below. However, when chemicals are produced using an organic solvent, equipment to recover the solvent must generally be provided. Thus, if a novel diol can be produced without a solvent, or using, as a reaction solvent, a solvent that does not require recovery equipment, the production equipment can be simplified, which is industrially beneficial.

Therefore, an object of the present invention is to solve such problems and provide a method for producing a diol that allows production without using an organic solvent as a reaction solvent.

Solution to Problem

As a result of an examination conducted by the present inventors on the basis of the above-mentioned problems, the present inventors solved the above-mentioned problems by the following means <1>, and preferably by the following means <2> to <12>.

<1> A method for producing a diol represented by Formula (1), the method including using water as a solvent to carry out a cyclodehydration reaction of a 1,4-cyclohexanedione derivative represented by Formula (2) below with a triol represented by Formula (3) below to produce the diol represented by Formula (1);

[Chemical Formula 1]

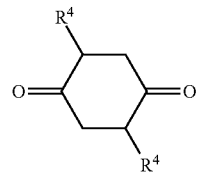

in Formula (2), $R^4$ each independently denotes a hydrogen atom, a heteroatom-containing group, a halogen atom-containing group, a linear alkyl group having from 1 to 6 carbon atoms, a branched alkyl group having from 3 to 6 carbon atoms, or a group including an aryl group and having from 6 to 12 carbon atoms;

[Chemical Formula 2]

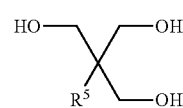

in Formula (3), $R^5$ denotes a hydrocarbon group; and

[Chemical Formula 3]

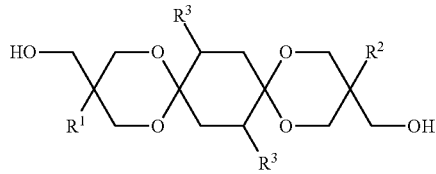

in Formula (1), $R^1$ and $R^2$ each independently denote a hydrocarbon group, and $R^3$ each independently denotes a hydrogen atom, a heteroatom-containing group, a halogen atom-containing group, a linear alkyl group having from 1 to 6 carbon atoms, a branched alkyl group having from 3 to 6 carbon atoms, or a group including an aryl group and having from 6 to 12 carbon atoms.

<2> The method for producing a diol according to <1>, wherein $R^4$ in Formula (2) is each independently a hydrogen atom, a linear alkyl group having from 1 to 6 carbon atoms, a branched alkyl group having from 3 to 6 carbon atoms, or a group including an aryl group and having from 6 to 12 carbon atoms.

<3> The method for producing a diol according to <1>, wherein $R^4$ in Formula (2) is each independently a hydrogen atom or a methyl group.

<4> The method for producing a diol according to any one of <1> to <3>, wherein $R^5$ in Formula (3) denotes a linear alkyl group having from 1 to 7 carbon atoms, a branched alkyl group having from 3 to 7 carbon atoms, or an aryl group.

<5> The method for producing a diol according to any one of <1> to <3>, wherein $R^5$ in Formula (3) is a linear alkyl group having from 1 to 7 carbon atoms or an aryl group.

<6> The method for producing a diol according to <1>, wherein $R^4$ in General Formula (2) is a hydrogen atom, and $R^5$ in Formula (3) is an ethyl group, a methyl group, or a phenyl group.

<7> The method for producing a diol according to any one of <1> to <6>, wherein the cyclodehydration reaction is carried out at a temperature of 80° C. or less.

<8> The method for producing a diol according to any one of <1> to <7>, wherein water is added as the solvent such that a theoretical yield of the diol represented by Formula (1), calculated from added amounts of the 1,4-cyclohexanedione derivative represented by Formula (2) and the triol represented by Formula (3), is 3 mass % or more of a total of the added amount of water as the solvent and the theoretical yield.

<9> The method for producing a diol according to any one of <1> to <8>, wherein the cyclodehydration reaction is carried out in the presence of an acid catalyst.

<10> The method for producing a diol according to <9>, wherein the acid catalyst contains at least one of methanesulfonic acid or para-toluenesulfonic acid.

<11> The method for producing a diol according to any one of <1> to <10>, wherein the 1,4-cyclohexanedione derivative represented by Formula (2) is 1,4-cyclohexanedione, and the triol represented by Formula (3) is at least one of trim ethylolpropane, trimethylolethane, or tris(hydroxymethyl)toluene.

<12> The method for producing a diol according to any one of <1> to <11>, further including filtering a reaction solution after the cyclodehydration reaction and adding to the filtrate a 1,4-cyclohexanedione derivative represented by Formula (2) and a triol represented by Formula (3) to carry out a cyclodehydration reaction once again.

Advantageous Effects of Invention

Through the present invention, a method for producing a diol that allows production without using an organic solvent as a reaction solvent can be provided.

DESCRIPTION OF EMBODIMENTS

The contents of the present invention will be described in detail below. Note that in the present specification, the phrase "from . . . to . . . " is used in a sense that includes the numerical values in the phrase as the lower and upper limit values.

The term (meth)acrylate means both acrylate and methacrylate. The same applies to terms such as (meth)acrylic acid.

The diol production method of the present invention is a method for producing a diol represented by General Formula (1), the method including using water as a solvent to carry out a cyclodehydration reaction of a 1,4-cyclohexanedione derivative represented by Formula (2) below with a triol represented by Formula (3) below to produce the diol represented by Formula (1).

[Chemical Formula 4]

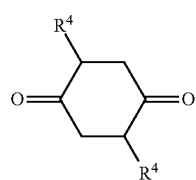

(2)

In Formula (2), $R^4$ each independently denotes a hydrogen atom, a heteroatom-containing group, a halogen atom-containing group, a linear alkyl group having from 1 to 6 carbon atoms, a branched alkyl group having from 3 to 6 carbon atoms, or a group including an aryl group and having from 6 to 12 carbon atoms.

[Chemical Formula 5]

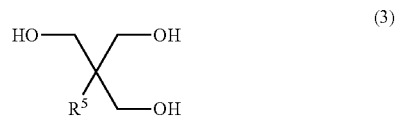

(3)

In Formula (3), $R^5$ denotes a hydrocarbon group.

[Chemical Formula 6]

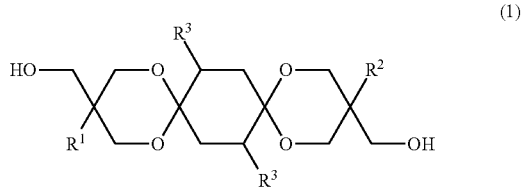

(1)

In Formula (1), $R^1$ and $R^2$ each independently denote a hydrocarbon group, and $R^3$ each independently denotes a hydrogen atom, a heteroatom-containing group, a halogen atom-containing group, a linear alkyl group having from 1 to 6 carbon atoms, a branched alkyl group having from 3 to 6 carbon atoms, or a group including an aryl group and having from 6 to 12 carbon atoms.

In the present invention, the 1,4-cyclohexanedione derivative represented by Formula (2) and the triol represented by Formula (3) are subjected to a cyclodehydration reaction using water as a solvent. Use of water as the reaction solvent achieves a production method that addresses environmental issues. Furthermore, the need for equipment to recover the organic solvent is eliminated, and thus such a production method is industrially advantageous.

In the present invention, the matter of carrying out a reaction using water as a solvent means that the most abundant component of the reaction solvents for the cyclodehydration reaction is water, and means that water accounts for preferably 80 mass % or more, more preferably 90 mass % or more, even more preferably 95 mass % or more, and yet even more preferably 98 mass % or more of the reaction solvents. Moreover, an example of an embodiment of the present invention is an aspect in which an organic solvent is not used aggressively as a reaction solvent. Not using an organic solvent aggressively means that an organic solvent is intentionally not used, and does not exclude the incorporated organic solvents, etc. as impurities from raw materials.

The water used in the cyclodehydration reaction of the present invention is preferably ion exchanged water, distilled water, RO water, or tap water, and ion exchanged water and distilled water are more preferable. One type of water may be used, or two or more types of waters may be used.

The reaction temperature of the cyclodehydration reaction of the present invention is, for example, 100° C. or less, preferably 80° C. or less, more preferably 70° C. or less, even more preferably 55° C. or less, and yet even more preferably 50° C. or less. Lowering the reaction temperature (in particular to 50° C. or less) allows the diol represented by Formula (1) to be easily precipitated in a slurry form, and facilitates separation and purification from the reaction product. The lower limit may be, for example, 10° C. or higher, 15° C. or higher, 30° C. or higher, 35° C. or higher, or 38° C. or higher.

Here, during the cyclodehydration reaction, the reaction solution is typically heated to a predetermined reaction temperature and the reaction is allowed to proceed. The reaction temperature of the cyclodehydration reaction refers to a temperature at which the reaction steadily proceeds, the temperature thereof being reached through the above-mentioned heating. For cases such as those in which the cyclodehydration reaction is carried out in a reactor, the temperature at which the reaction steadily proceeds may fluctuate, but through heating and stirring, the temperature changes can be adjusted to within 20° C., preferably within 15° C., and more preferably within 10° C. In the present invention, the reaction temperature of the cyclodehydration reaction is, for example, a temperature at any location in the reactor during the progression of the cyclodehydration reaction, and preferably, the highest temperature among the temperatures in the reactor during the progression of the cyclodehydration reaction is lower than or equal to the upper limit of the above-mentioned reaction temperature, and the lowest temperature is higher than or equal to the lower limit of the above-mentioned reaction temperature.

Furthermore, the reaction pressure of the cyclodehydration reaction is not particularly limited as long as the reaction pressure is such that the cyclodehydration reaction proceeds at the above-mentioned reaction temperature, and it may be normal pressure. In some cases, it is also effective to carry out the reaction under reduced pressure. The atmosphere surrounding the reaction system during this reaction is not particularly limited, and for example, the reaction may be carried out in any of an air atmosphere, a nitrogen atmosphere, or under a flow of nitrogen. The reaction duration may be appropriately adjusted depending on the amount of catalyst and the reaction temperature, but ordinarily, the reaction is preferably carried out for 2 to 48 hours, and more preferably for 5 to 20 hours.

In the present invention, as a solvent, water is preferably added such that the theoretical yield of the diol represented by Formula (1), calculated from the added amounts of the 1,4-cyclohexanedione derivative represented by Formula (2) and the triol represented by Formula (3), is 3 mass % or more of the total of the added amount of water as the solvent and the theoretical yield, and the theoretical yield is more preferably greater than 5 mass %, even more preferably 7 mass % or more, yet even more preferably 10 mass % or more, yet even more preferably 15 mass % or more, and yet even more preferably 18 mass % or more. When the theoretical yield increases, that is, when the concentration of the reaction solution is increased, the diol represented by Formula (1) is easily precipitated in a slurry form, and separation and purification are facilitated. Furthermore, the water as the solvent is preferably used in a range such that the theoretical yield is 50 mass % or less, more preferably 45 mass % or less, and even more preferably 40 mass % or less, and the theoretical yield may be 35 mass % or less.

The theoretical yield refers to the maximum amount of the diol represented by Formula (1) that can be theoretically obtained from the added amounts of the raw materials, namely the 1,4-cyclohexanedione derivative represented by Formula (2) and the triol represented by Formula (3).

In the cyclodehydration reaction of the present invention, the usage amount of the triol represented by Formula (3) relative to the usage amount of the 1,4-cyclohexanedione derivative represented by Formula (2) is not particularly limited as long as it is an amount at which the diol having a desired dispiro structure can be produced. However, since it is industrially advantageous to minimize the unreacted component, the lower limit of the usage amount of the triol represented by Formula (3) relative to the usage amount of the 1,4-cyclohexanedione derivative represented by Formula (2) is, on a molar basis, preferably 2.00 equivalents or more, more preferably 2.05 equivalents or more, even more preferably 2.08 equivalents or more, and yet even more preferably 2.10 equivalents or more. The upper limit of the usage amount is preferably 5.00 equivalents or less, more preferably 3.00 equivalents or less, even more preferably 2.50 equivalents or less, and yet even more preferably 2.30 equivalents or less.

The cyclodehydration reaction (acetalization reaction) of the present invention is preferably carried out in the presence of an acid catalyst. The acid catalyst is not particularly limited, and a known acid catalyst may be used. Specific examples of such acid catalysts that can be used include organic acids such as paratoluenesulfonic acid and methanesulfonic acid, mineral acids such as hydrochloric acid, sulfuric acid, nitric acid, and phosphoric acid, and solid acid catalysts such as Nafion (Sigma-Aldrich Corporation, trade name), and cation exchange resins. However, in the present invention, since the reaction product is normally precipitated in the reaction solution as a solid, organic acids or mineral acids are preferably used from the perspective of ease of post-treatment of the reaction. In particular, organic acids are preferable as the acid catalyst that is used in the present invention. In addition, the acid catalyst is preferably a homogeneous acid catalyst. Furthermore, the acid catalyst may also be a hydrate.

In the present invention, the acid catalyst preferably includes at least one of methanesulfonic acid, paratoluenesulfonic acid, sulfuric acid, hydrochloric acid, nitric acid, or phosphoric acid, more preferably includes at least one of methanesulfonic acid, paratoluenesulfonic acid, or sulfuric acid, and even more preferably includes at least one of methanesulfonic acid or paratoluenesulfonic acid. Two or more types of acid catalysts may be used in combination.

The usage amount of the acid catalyst is not particularly limited, but is, on a molar basis, preferably from 0.00001 to 0.1 equivalents relative to the amount of the 1,4-cyclohexanedione derivative represented by Formula (2). From the perspective of reaction duration, the usage amount of the acid catalyst is more preferably 0.00005 equivalents or more and even more preferably 0.0001 equivalents or more, and from the perspectives of suppressing the generation of by-products and removing the catalyst, the usage amount is more preferably 0.1 equivalents or less and even more preferably 0.05 equivalents or less.

In the present invention, after the cyclodehydration reaction, the reaction solution is filtered, and the filtered material is preferably washed with water. In the present invention, the solubility in water of the raw materials (the 1,4-cyclohexanedione derivative represented by Formula (2) and the triol represented by Formula (3)) is high, and the solubility of the product diol represented by Formula (I) is low, and therefore when the cyclodehydration reaction is allowed to proceed using water as a solvent, the product diol represented by Formula (1) can be precipitated as a solid. When precipitated as a solid, the diol represented by Formula (1) can be easily separated and purified. The filtration temperature is not particularly defined, and can be arbitrarily defined, for example, in a range of from 10 to 100° C. From the perspective of production efficiency, it is industrially preferable, for example, to carry out filtration at around the reaction temperature (for example, a range from the reaction temperature to the reaction temperature—20° C.). Furthermore, filtration may be carried out after cooling from the reaction temperature to room temperature (for example, from 10 to 45° C.).

Therefore, the diol production method of the present invention more preferably includes filtering the reaction solution after the cyclodehydration reaction, washing the filtered material after filtration, and separating the diol represented by Formula (1). Furthermore, when an acid catalyst is used as the reaction catalyst, neutralizing may also be included. An alkali such as caustic soda, for example, can be used for neutralization.

In the present invention, for example, the solubility of the 1,4-cyclohexanedione derivative represented by Formula (2) and the solubility of the triol represented by Formula (3) in 25° C. water can each be 100 g/L or higher (preferably, from 100 to 1000 g/L), and the solubility of the diol represented by Formula (1) in water at 25° C. can be 0.5 g/L or less (preferably from 0.0001 to 0.5 g/L).

In the present invention, a difference between the solubility in 25° C. water of the component with the lowest solubility in the raw materials (the 1,4-cyclohexanedione derivative represented by Formula (2) and the triol represented by Formula (3)), and the solubility in 25° C. water of the diol represented by Formula (1) (in a case where a plurality of types of diols are synthesized, then the component with the highest solubility) is preferably 90 g/L or higher. Such a range further facilitates separation and purification of the product diol represented by Formula (1).

Note that, in the present invention, it is not necessary to precipitate, as a solid, the diol represented by Formula (1), and as illustrated in the examples described below, the diol may be produced under conditions at which almost no slurry is produced.

The diol obtained by the production method of the present invention can be isolated by known purification methods after appropriate post-treatments such as neutralization, filtration (preferably rinsing with water), washing, and concentration. Specific examples include crystallization, distillation, adsorption treatment, column chromatography, preparative HPLC (liquid chromatography), and preparative gas chromatography. Furthermore, depending on the application of the next reaction, the diol can be subjected to only the post-treatment of the production method of the present invention and used in an unpurified state, particularly without carrying out an isolation operation.

In the production method of the present invention, the purity of the obtained diol represented by Formula (1) as determined through GC analysis (HPLC analysis when measurement with GC analysis is difficult) can be 95 mass % or higher. Furthermore, the isolation yield of the obtained diol represented by Formula (1) can be 90 mass % or highen The present invention also includes an embodiment in which after the cyclodehydration reaction, the reaction solution (slurry liquid) is filtered, the 1,4-cyclohexanedione derivative represented by Formula (2) and the triol represented by Formula (3) are added to the filtrate, and the cyclodehydration reaction is carried out once again. In the present embodiment, after the reaction solution (reaction slurry liquid) is filtered, water may be added to the filtrate as necessary in addition to the 1,4-cyclohexanedione derivative represented by Formula (2) and the triol represented by Formula (3). Furthermore, an acid catalyst may be added together with the water. In this manner, the filtration mother liquor is recycled as is to the next reaction, and thereby an advantage of enabling reuse without providing a step of recovering the unreacted raw material remaining in the mother liquor is provided.

Next, the 1,4-cyclohexanedione derivative represented by Formula (2) and used in the present invention will be described.

[Chemical Formula 7]

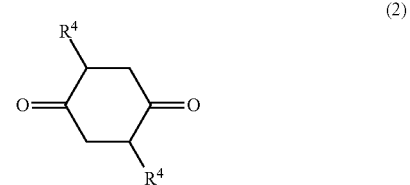

(2)

In Formula (2), $R^4$ each independently denotes a hydrogen atom, a heteroatom-containing group, a halogen atom-containing group, a linear alkyl group having from 1 to 6 carbon atoms, a branched alkyl group having from 3 to 6 carbon atoms, or a group including an aryl group and having from 6 to 12 carbon atoms.

$R^4$ in Formula (2) each independently denotes a hydrogen atom, a heteroatom-containing group, a halogen atom-containing group (preferably, a halogen atom), a linear alkyl group having from 1 to 6 carbon atoms, a branched alkyl group having from 3 to 6 carbon atoms, or a group including an aryl group and having from 6 to 12 carbon atoms; and is preferably a hydrogen atom, a linear alkyl group having from 1 to 6 carbon atoms, a branched alkyl group having from 3 to 6 carbon atoms, or a group including an aryl group and having from 6 to 12 carbon atoms, is more preferably a hydrogen atom, a linear alkyl group having from 1 to 6 carbon atoms, or a branched alkyl group having from 3 to 6 carbon atoms, is even more preferably a hydrogen atom or a methyl group, and is yet even more preferably a hydrogen atom.

Examples of the heteroatom included in the heteroatom-containing group include an oxygen atom, a sulfur atom, and a nitrogen atom.

Preferable examples of the heteroatom-containing group include alkoxy groups, alkyl thioether groups, amino groups, and nitro groups. In addition, the alkyl chain constituting the alkoxy group or the alkyl thioether group is preferably a linear alkyl chain having from 1 to 6 carbon atoms, and is more preferably a linear alkyl chain having from 1 to 3 carbon atoms.

The linear alkyl group having from 1 to 6 carbon atoms is preferably a linear alkyl group having from 1 to 5 carbon atoms, more preferably a linear alkyl group having from 1 to 3 carbon atoms, and even more preferably a methyl group or an ethyl group.

The branched alkyl group having from 3 to 6 carbon atoms is preferably a branched alkyl group having from 3 to 5 carbon atoms, more preferably a branched alkyl group having 3 or 4 carbon atoms, and even more preferably a branched alkyl group having 3 carbon atoms.

The group including an aryl group and having from 6 to 12 carbon atoms is preferably a phenyl group or an alkyl group substituted with a phenyl group, and is more preferably a phenyl group. The number of carbon atoms of the alkyl group constituting the alkyl group substituted with a phenyl group is preferably from 1 to 3, more preferably 1 or 2, and even more preferably 1.

Examples of $R^4$ in Formula (2) include a hydrogen atom, a methyl group, ethyl group, n-propyl group, isopropyl group, n-butyl group, 1-methylpropyl group, 2-methylpropyl group, 1,1-dimethyl ethyl group (tert-butyl group), n-pentyl group, 1-methylbutyl group, 2-methylbutyl group, 3-methylbutyl group, 1-ethylpropyl group, 1,1-dimethylpropyl group, 1,2-dimethylpropyl group, 2,2-dimethylpropyl group (neopentyl group), n-hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl group, 2-ethylbutyl group, 1,1,2-trimethyl propyl group, 1,2,2-trimethylpropyl group, 1-ethyl-1-methylpropyl group, 1-ethyl-2-methylpropyl group, a fluorine atom, chlorine atom, bromine atom, iodine atom, methoxy group, ethoxy group, propyloxy group, butoxy group, methyl thioether group, ethyl thioether group, amino group, nitro group, phenyl group, and benzyl group.

Among these, $R^4$ is more preferably a hydrogen atom, a methyl group, an ethyl group, an n-propyl group, an isopropyl group, or an n-butyl group. Furthermore, from the perspective of ease of industrial procurement, $R^4$ is particularly preferably a hydrogen atom.

The method for producing the 1,4-cyclohexanedione derivative represented by Formula (2) and used in the present invention is not particularly limited, and a 1,4-cyclohexanedione derivative produced by a known method can be used. For example, Organic Syntheses, Coll. Vol. 5, p. 288 (1973) and Vol. 45, p. 25 (1965) reports a two-step synthesis process of 1,4-cyclohexanedione from a succinic acid diester. In addition, J. Chem. Soc., Perkin Trans. 1, 1979, p. 3095 describes a synthesis process of 1,4-cyclohexanedione derivatives in which an alkyl group is introduced into the alpha position of a carbonyl. For more convenient applications, a product that is distributed as an industrial product may be purified and used, or may be used in an unpurified state.

The present inventors attempted a study similar to the present invention using cyclohexanedione isomers (1,2-isomer, 1,3-isomer) besides 1,4-cyclohexanedione. As a result, the generation of a 1,2-dispiro form and a 1,3-dispiro form corresponding to each isomer was confirmed, but the reaction yield was significantly low. A similar case is also described in paragraph [0021] of WO 2016/052476, and therefore in the present invention, the use of a 1,4-cyclohexanedione derivative as a raw material for a diol having a dispiro structure is preferred in order to industrially and easily obtain a high yield.

The 1,4-cyclohexanedione derivative represented by Formula (2) is preferably 1,4-cyclohexanedione.

One type of 1,4-cyclohexanedione derivative represented by Formula (2) may be used alone, or two or more types may be used.

Next, the triol represented by Formula (3) will be described.

[Chemical Formula 8]

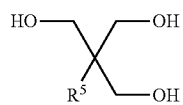

(3)

In Formula (3), $R^5$ denotes a hydrocarbon group. However, the hydrocarbon group as $R^5$ does not contain an ether bond.

The $R^5$ in Formula (3) is a hydrocarbon group, and preferably denotes a linear alkyl group having from 1 to 7 carbon atoms, a branched alkyl group having from 3 to 7 carbon atoms or an aryl group, more preferably denotes a linear alkyl group having from 1 to 7 carbon atoms or an aryl group, and even more preferably a linear alkyl group having from 1 to 7 carbon atoms.

An example of a preferred embodiment of $R^5$ in the present invention is an ethyl group, a methyl group, or a phenyl group. In this case, $R^4$ in Formula (2) is preferably a hydrogen atom.

The linear alkyl group having from 1 to 7 carbon atoms is preferably a linear alkyl group having from 1 to 5 carbon atoms, more preferably a linear alkyl group having from 1 to 3 carbon atoms, and even more preferably a methyl group or an ethyl group.

The branched alkyl group having from 3 to 7 carbon atoms is preferably a branched alkyl group having from 3 to 5 carbon atoms, more preferably a branched alkyl group having 3 or 4 carbon atoms, and even more preferably a branched alkyl group having 3 carbon atoms.

The aryl group is preferably an aryl group having from 6 to 20 carbon atoms, more preferably an aryl group having from 6 to 14 carbon atoms, and even more preferably a phenyl group, a naphthyl group, or an anthracenyl group, and a phenyl group is yet even more preferable.

Examples of $R^5$ in Formula (3) include a methyl group, ethyl group, n-propyl group, isopropyl group, n-butyl group, 1-methylpropyl group, 2-methylpropyl group, 1,1-dimethyl ethyl group (tert-butyl group), n-pentyl group, 1-methylbutyl group, 2-methylbutyl group, 3-methylbutyl group, 1-ethylpropyl group, 1,1-dimethylpropyl group, 1,2-dimethylpropyl group, 2,2-dimethylpropyl group (neopentyl group), n-hexyl group, 1-methylpentyl group, 2-methylpentyl group, 3-methylpentyl group, 4-methylpentyl group, 1,1-dimethylbutyl group, 1,2-dimethylbutyl group, 1,3-dimethylbutyl group, 2,2-dimethylbutyl group, 2,3-dimethylbutyl group, 3,3-dimethylbutyl group, 1-ethylbutyl group, 2-ethylbutyl group, 1,1,2-trimethyl propyl group, 1,2,2-trimethylpropyl group, 1-ethyl-1-methylpropyl group, 1-ethyl-2-methylpropyl group, n-heptyl group, 1-methylhexyl group, 2-methylhexyl group, 3-methylhexyl group, 4-methylhexyl group, 5-methylhexyl group, 1,1-dimethylpentyl group, 1,2-dimethylpentyl group, 1,3-dimethylpentyl group, 1,4-dimethylpentyl group, 1,5-dimethylpentyl group, 2,2-dimethylpentyl group, 2,3-dimethylpentyl group, 2,4-dimethylpentyl group, 3,3-dimethylpentyl group, 3,4-dimethylpentyl group, 4,4-dimethylpentyl group, 1-ethylpentyl group, 2-ethylpentyl group, 3-ethylpentyl group, 1-propylbutyl group, 2-propylbutyl group, 3-propylbutyl group, 1-ethyl-1-methylbutyl group, 1-ethyl-2-methylbutyl group, 1-ethyl-3-methylbutyl group, 2-ethyl-1-methylbutyl group, 2-ethyl-2-methylbutyl group, 2-ethyl-3-methylbutyl group, 1,2,3-trimethylbutyl group, phenyl group, naphthyl group, and anthracenyl group.

Among these, $R^5$ is more preferably a methyl group, an ethyl group, an n-propyl group, an isopropyl group, an n-butyl group, or a phenyl group, and is even more preferably a methyl group, an ethyl group, or a phenyl group.

The triol represented by Formula (3) is preferably at least one of trimethylolpropane, trimethylolethane, or tris(hydroxymethyl)toluene.

One type of triol represented by Formula (3) may be used alone, or two or more types may be used.

In the present invention, a particularly preferable case is one in which the 1,4-cyclohexanedione derivative represented by Formula (2) is 1,4-cyclohexanedione, and the triol represented by Formula (3) is at least one of trimethylolpropane, trimethylolethane, or tris(hydroxymethyl)toluene (preferably, at least one of trimethylolpropane or trimethylolethane).

Next, the diol represented by Formula (1) will be described.

[Chemical Formula 9]

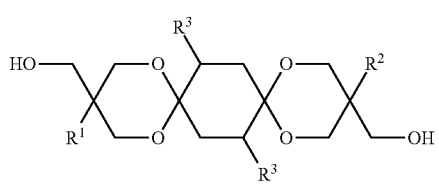

(1)

In Formula (1), $R^1$ and $R^2$ each independently denote a hydrocarbon group, and $R^3$ each independently denotes a hydrogen atom, a heteroatom-containing group, a halogen atom-containing group, a linear alkyl group having from 1 to 6 carbon atoms, a branched alkyl group having from 3 to 6 carbon atoms, or a group including an aryl group and having from 6 to 12 carbon atoms.

A diol excelling in thermal stability can be obtained by such configuration of the diol. Furthermore, the diol represented by Formula (1) ordinarily tends to have a lower melting point than spiroglycol, and exhibits high handling ease. Furthermore, a rigid material is obtained by the structure represented by Formula (1).

The melting point of the diol represented by Formula (1) of the present invention can be, for example, 220° C. or less, and further can be 218° C. or less, 200° C. or less, and 180° C. or less. The lower limit of the melting point of the diol represented by Formula (1) is not particularly defined, and the diol sufficiently excels in handling ease even when the melting point is, for example, 150° C. or higher, or 160° C. or higher.

In addition, the diol represented by Formula (1) of the present invention has a neo structure in which a hydrogen atom is not present at the beta position of the two hydroxyl groups, and has an advantage that the generation of olefins due to (3-elimination is essentially unlikely to occur.

The diol represented by Formula (1) may have a plurality of geometric isomers attributed to two 6-membered ring acetal structures, and indicates any one or a mixture of a plurality of the geometric isomers in the present invention. Also, the conformation of each of the three consecutive 6-membered ring structures is not defined, and any possible conformation can be freely taken. The production ratio of the geometric isomers of the diols represented by Formula (1) varies depending on the reaction conditions (type of reaction solvent, type of reaction catalyst, and the reaction temperature) and the like, and is not particularly limited. The mixture of geometric isomers of diols having the dispiro structure obtained in the present invention can be used as a mixture or separated into each geometric isomer by known methods.

In Formula (1), $R^1$ and $R^2$ may be the same or different, and are synonymous with $R^5$ in Formula (3), and the preferred ranges are also the same. In addition, from the perspective of enabling a particularly convenient production method, $R^1$ and $R^2$ are preferably the same, and an aspect in which $R^1$ and $R^2$ are the same, and are a methyl group, an ethyl group, or a phenyl group is more preferable.

In Formula (1), $R^3$ may be the same or different, and are synonymous with $R^4$ in Formula (2), and the preferred ranges are also the same.

An example of a preferred embodiment of the diol represented by Formula (1) is a diol in which $R^1$ and $R^2$ in Formula (1) are each independently an ethyl group, a methyl group, or a phenyl group, and $R^3$ is a hydrogen atom.

Diols preferably used in the present invention are presented below. Of course, the present invention is not limited to these diols. Note that Me represents a methyl group, Et represents an ethyl group, Pr represents a propyl group, and Bu represents a butyl group.

[Chemical Formula 10]

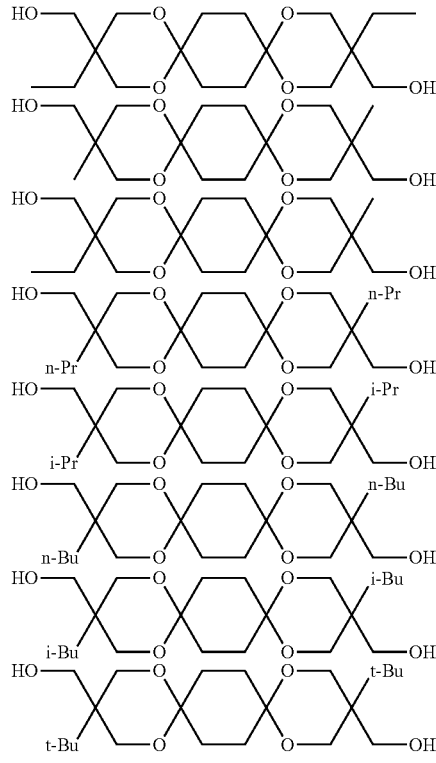

[Chemical Formula 11]

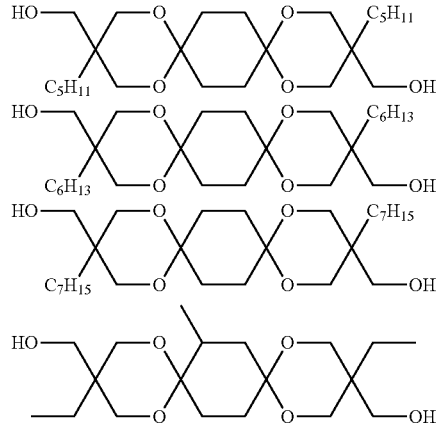

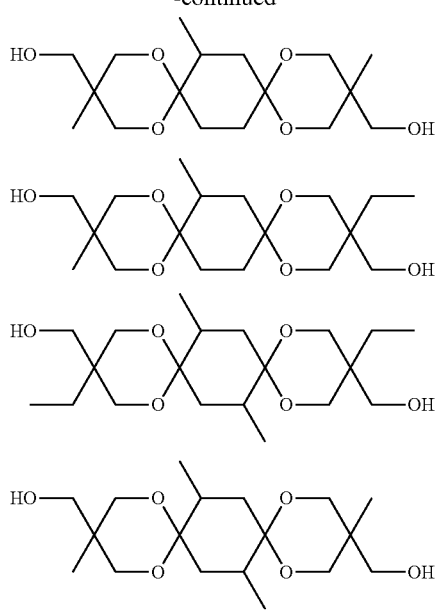
[Chemical Formula 12]
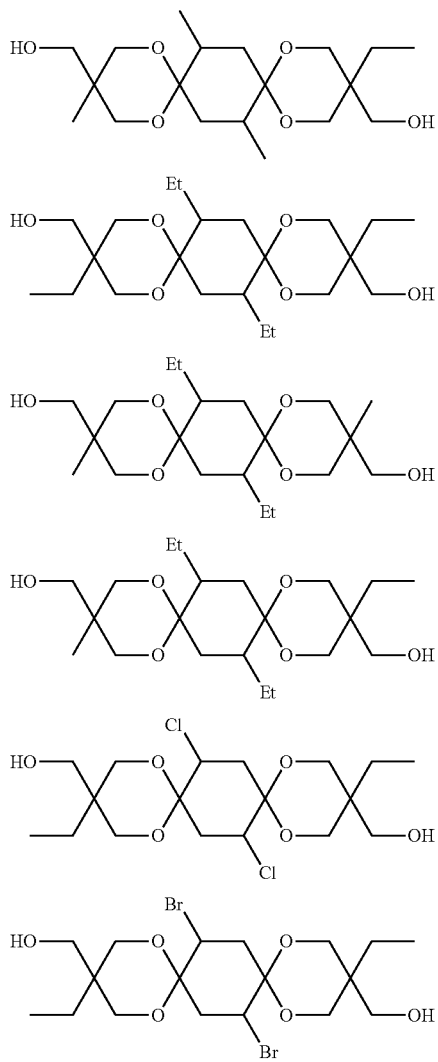
[Chemical Formula 13]
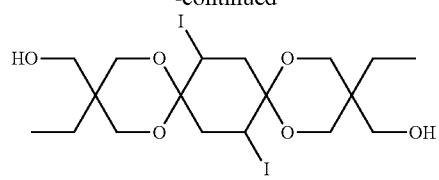
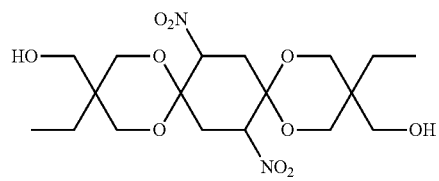
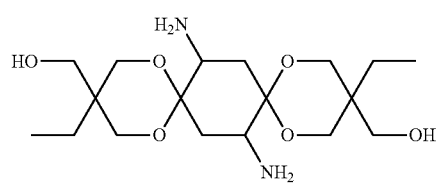
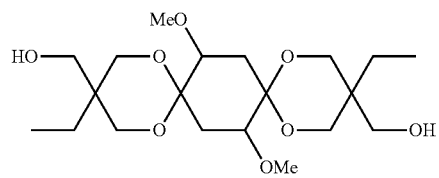
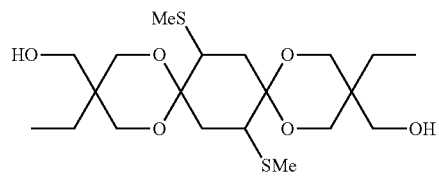
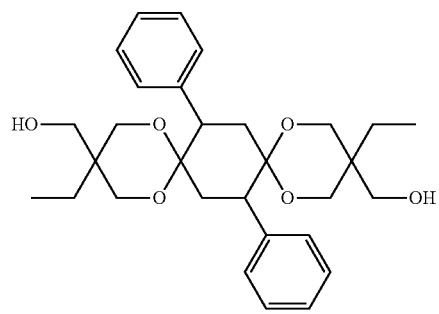
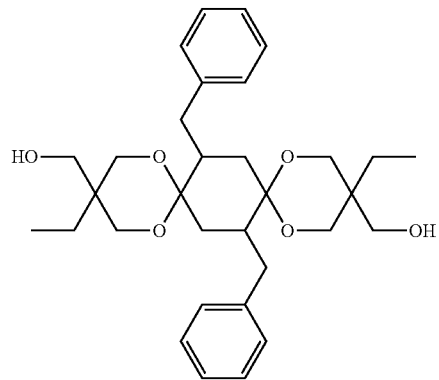

[Chemical Formula 14]

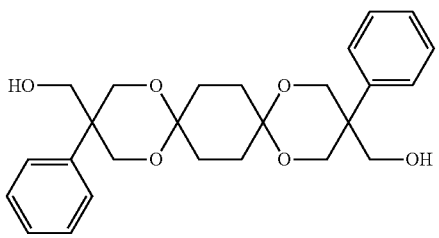

The molecular weight of the diol represented by Formula (1) is preferably from 300 to 550, and more preferably from 300 to 500.

The diol of the present invention can be used as a raw material for various industrial materials. For example, the diol of the present invention can be used as a raw material of a thermoplastic resin or as a raw material of a (meth) acrylate.

The (meth)acrylate may be a monofunctional (meth) acrylate having one (meth)acryloyloxy group, or a di(meth) acrylate having two (meth)acryloyloxy groups.

The di(meth)acrylate can be used as a reactive diluent or a viscosity modifier in applications such as paints, coating agents, hard coating agents, inks, adhesives, tacky adhesives, resist materials, molding materials, and surface processing agents.

EXAMPLES

The present invention will be described more specifically below through examples, but the present invention is not particularly limited by the following examples. Unless otherwise indicated, the notation of "%" in the examples is on a mass basis.

The method for analyzing physical properties and the like in the examples is as follows.

Reaction Yield and Product Purity

The reaction yield and product purity were determined by gas chromatography (GC, instrument name: Agilent 6850, available from Agilent Technologies, Inc.) or high performance liquid chromatography (HPLC, instrument name: Chromaster, available from Hitachi High-Tech Science Corporation) through the internal standard method.

Example 1

A 5-liter round bottom separable flask was charged with 360 g of 1,4-cyclohexanedione (reagent available from Tokyo Chemical Industry Co., Ltd., solubility in water at 25° C. of 750 g/L), 905 g of trimethylolpropane (available from Mitsubishi Gas Chemical Co., Inc., solubility in water at 25° C. of 100 g/L or higher), 2500 g of ion exchanged water (30 mass % equivalent relative to the theoretical yield of a compound A) (means that the percentage (in mass %) of the theoretical yield to the total of the added amount of water and the theoretical yield is 30 mass % equivalent, similarly considered in the following examples), and 6.17 g of methanesulfonic acid (reagent available from Tokyo Chemical Industry Co., Ltd.), and the mixture is heated and stirred under normal pressure such that the temperature inside the flask was 40° C. to 50° C. and a cyclodehydration reaction was carried out. At the initial stage of the reaction, all of the raw materials were completely dissolved, and a clear and homogeneous solution was formed, but as the reaction proceeded, the product began to precipitate in a slurry form. The slurry liquid was then heated and stirred at that temperature for 7 hours. After the reaction slurry liquid was cooled to 25° C., the product was collected as a wet cake through a filtration operation. Furthermore, the reaction solution contained in the wet cake was flushed with 260 g of water. The reaction filtrate at this stage was 1900 g. The obtained wet cake was neutralized by passing aqueous caustic soda through the wet cake, after which the wet cake was rinsed with water and vacuum dried, and thereby 884 g of a compound A (GC purity: 99.2%, isolation yield: 80%) was obtained. The solubility in water at 25° C. of the obtained compound A was 0.5 g/L or less.

The reaction scheme of Example 1 is shown below.

[Chemical Formula 15]

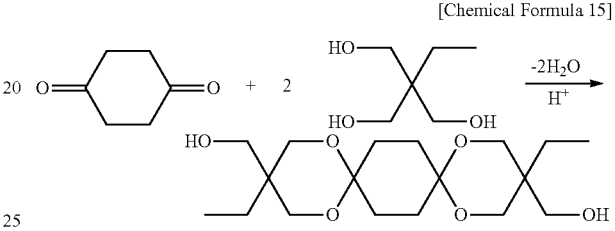

Example 2 (Reaction Filtrate Recycling Experiment 1)

To a 5-liter separable flask, 1900 g of the reaction filtrate obtained in Example 1 was returned, and a recycling reaction was carried out. The 5-liter separable flask was additionally charged with 360 g of 1,4-cyclohexanedione (reagent available from Tokyo Chemical Industry Co., Ltd.), 905 g of trimethylolpropane (available from Mitsubishi Gas Chemical Co., Inc.), 900 g of ion exchanged water, and 0.62 g of methanesulfonic acid (reagent available from Tokyo Chemical Industry Co., Ltd.), and similar to Example 1, the mixture was heated and stirred under normal pressure such that the temperature inside the flask was 40° C. to 50° C. and a cyclodehydration reaction was carried out. After stirring for 13.5 hours, the reaction slurry liquid was cooled to 25° C., and the product was collected as a wet cake through a filtration operation. Furthermore, the reaction solution contained in the wet cake was flushed with 400 g of water. The reaction filtrate at this stage was 2300 g. The obtained wet cake was neutralized by passing aqueous caustic soda through the wet cake, after which the wet cake was rinsed with water and vacuum dried, and thereby 1155 g of the compound A (GC purity: 99.5%, isolation yield combined with Example 1: 92%) was obtained.

Example 3 (Reaction Filtrate Recycling Experiment 2)

To a 5-liter separable flask, 2300 g of the reaction filtrate obtained in Example 2 was returned, and a second recycling reaction was carried out. The 5-liter separable flask was additionally charged with 360 g of 1,4-cyclohexanedione (reagent available from Tokyo Chemical Industry Co., Ltd.), 905 g of trimethylolpropane (available from Mitsubishi Gas Chemical Co., Inc.), 400 g of ion exchanged water, and 0.62 g of methanesulfonic acid (reagent available from Tokyo Chemical Industry Co., Ltd.), and similar to Example 1, the mixture was heated and stirred under normal pressure such that the temperature inside the flask was 40° C. to 50° C. and a cyclodehydration reaction was carried out. After stirring for 11.5 hours, the reaction slurry liquid was cooled to 25° C., and the product was collected as a wet cake through a filtration operation. Furthermore, the reaction solution contained in the wet cake was flushed with 400 g of water. The reaction filtrate at this stage was 2300 g. The obtained wet cake was neutralized by passing aqueous caustic soda through the wet cake, after which the wet cake was rinsed with water and vacuum dried, and thereby 996 g of the compound A (GC purity: 99.5%, isolation yield combined with Example 1: 91%) was obtained.

Example 4

A cyclodehydration reaction was carried out for 3 hours under the same conditions as in Example 1 with the exception that 905 g of trimethylolpropane was changed to 810 g of trimethylolethane (available from Mitsubishi Gas Chemical Co., Inc., solubility in water at 25° C. of 100 g/L or higher), and the amount of ion exchanged water was reduced from 2500 g to 900 g. The amount of a compound B obtained after vacuum drying was 684 g (GC purity: 98.4%, isolation yield: 67%). The reaction scheme of Example 4 is shown below. The solubility of the obtained compound B in water at 25° C. was 0.5 g/L or less.

[Chemical Formula 16]

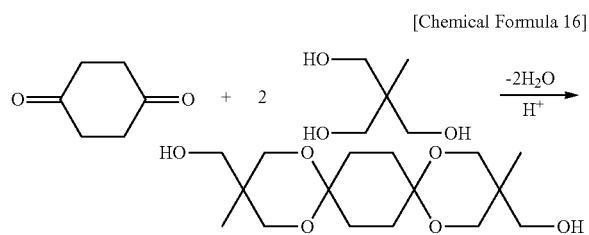

Example 5

A 30-liter flask was charged with 1.44 kg of 1,4-cyclohexanedione (reagent available from Tokyo Chemical Industry Co., Ltd.), 3.53 kg of trimethylolpropane (available from Mitsubishi Gas Chemical Co., Inc.), 17.2 kg of ion exchanged water (20 mass % equivalent relative to the theoretical yield of the compound A), and 24.7 g of methanesulfonic acid (reagent available from Tokyo Chemical Industry Co., Ltd.), and the mixture was heated and stirred under normal pressure such that the temperature inside the flask was 40° C. to 50° C. and a cyclodehydration reaction was carried out. At the initial stage of the reaction, all of the raw materials were completely dissolved, and a clear and homogeneous solution was formed, but as the reaction proceeded, the product began to precipitate in a slurry form. The slurry liquid was then heated and stirred at that temperature for 8 hours. After the reaction slurry liquid was cooled to 25° C., the product was collected as a wet cake through a filtration operation. The obtained wet cake was neutralized by passing aqueous caustic soda through the wet cake, after which the wet cake was rinsed with water and vacuum dried, and thereby 2.34 kg of the compound A (GC purity: 99.2%, isolation yield: 52%) was obtained.

Example 6

A reaction was carried out under the same conditions as in Example 1 with the exception that the reaction temperature was set to a range of from 85 to 90° C. The product slurry did not precipitate even after heating and stirring for 20 hours, but when the reaction solution was analyzed by GC, production of the compound A (GC yield: 15.7%) was confirmed.

Example 7

A 1-liter round bottom separable flask was charged with 10 g of 1,4-cyclohexanedione (reagent available from Tokyo Chemical Industry Co., Ltd.), 25 g of trimethylolpropane (available from Mitsubishi Gas Chemical Co., Inc.), 580 g of ion exchanged water (5 mass % equivalent relative to the theoretical yield of the compound A), and 0.17 g of methanesulfonic acid (reagent available from Tokyo Chemical Industry Co., Ltd.), and the mixture was heated and stirred under normal pressure such that the temperature inside the flask was 40° C. to 50° C. and a cyclodehydration reaction was carried out. After all the raw materials were completely dissolved to form a clear and homogeneous solution, the solution was subsequently heated and stirred for 20 hours, but almost no slurry was produced. The reaction solution was then subjected to GC analysis, and production of the compound A (GC yield: 18.0%) was confirmed.

Example 8

A 100 mL round bottom flask was charged with 1.51 g of 1,4-cyclohexanedione (reagent available from Tokyo Chemical Industry Co., Ltd.), 5.0 g of $\alpha,\alpha,\alpha$-tris(hydroxymethyl)toluene (available from Toronto Research Chemicals Inc.), 6.0 g of ion exchanged water, and 0.04 g of methanesulfonic acid (reagent available from Tokyo Chemical Industry Co., Ltd.), and the mixture was heated and stirred under normal pressure such that the temperature inside the flask was 25° C. to 30° C. and a cyclodehydration reaction was carried out. At the initial stage of the reaction, all of the raw materials were completely dissolved, and a clear and homogeneous solution was formed, but as the reaction proceeded, the product began to precipitate in a slurry form. The slurry liquid was then heated and stirred at that temperature for 24 hours. After the reaction slurry liquid was cooled to 25° C., the product was collected as a wet cake through a filtration operation. Furthermore, the reaction solution contained in the wet cake was flushed with 30 g of water. The obtained wet cake was neutralized by passing aqueous caustic soda through the wet cake, after which the wet cake was rinsed with water and vacuum dried, and thereby 2.7 g of a compound D (HPLC purity: 60%, isolation yield: 27%) was obtained.

[Chemical Formula 17]

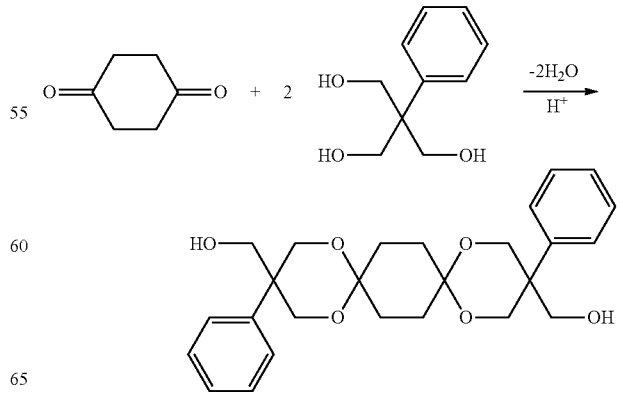

Example 9

The same procedures as those of Example 1 were carried out with the exception that the methanesulfonic acid in Example 1 was changed to an equimolar amount of para-toluenesulfonic acid monohydrate (special reagent available from FujiFilm Wako Pure Chemical Industries, Ltd.). The compound A was obtained in the same manner as in Example 1.

Example 10

A 300 mL flask was charged with 20 g of 1,4-cyclohexanedione (reagent available from Tokyo Chemical Industry Co., Ltd.), 25.1 g of trimethylolpropane (available from Mitsubishi Gas Chemical Co., Inc.), 22.5 g of trimethylolethane (available from Mitsubishi Gas Chemical Co., Inc.), 100 g of ion exchanged water (35 mass % equivalent relative to the theoretical yield for a case in which the entirety was the compound C), and 0.34 g of methanesulfonic acid (reagent available from Tokyo Chemical Industry Co., Ltd.), and the mixture was heated and stirred under normal pressure such that the temperature inside the flask became 40° C. to 50° C. and a cyclodehydration reaction was carried out. At the initial stage of the reaction, all of the raw materials were completely dissolved, and a clear and homogeneous solution was formed, but as the reaction proceeded, the product began to precipitate in a slurry form. The slurry liquid was then heated and stirred at that temperature for 3 hours. After the reaction slurry liquid was cooled to 25° C., the product was collected as a wet cake through a filtration operation. The obtained wet cake was neutralized by passing aqueous caustic soda through the wet cake, after which the wet cake was rinsed with water, and vacuum dried, and thereby 16.0 g (GC purity: 98.0%, compound A: compound B: compound C=62:2:36 (GC area ratio), yield: 27%) were obtained.

[Chemical Formula 18]

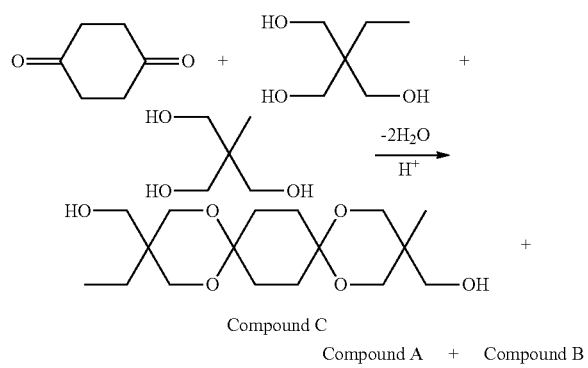

Compound C

Compound A + Compound B

INDUSTRIAL APPLICABILITY

The diols having a dispiro structure obtained in the present invention tend to have a higher thermal stability and a lower melting point than spiroglycol, and exhibit improved handling ease. Therefore, in the production of various resins (thermoplastic resins) using a diol component as a raw material, improvements in production efficiency and workability are anticipated. In addition, the diols of the present invention are monomer diols having a rigid structure, and therefore improvements in the physical properties (high hardness, abrasion resistance, transparency, heat resistance, weather resistance, and optical properties) of the various resins (thermoplastic resins) that are obtained can also be expected. Thus, the industrial applicability of the present invention is significant.

The invention claimed is:

1. A method for producing a diol represented by Formula (1), the method comprising using water as a solvent to carry out a cyclodehydration reaction of a 1,4-cyclohexanedione derivative represented by Formula (2) below with a triol represented by Formula (3) below to produce the diol represented by Formula (1);

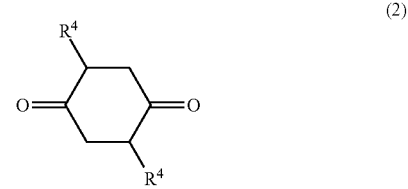

wherein $R^4$ each independently denotes at least one selected from the group consisting of a hydrogen atom, a heteroatom-containing group, a halogen atom-containing group, a linear alkyl group having from 1 to 6 carbon atoms, a branched alkyl group having from 3 to 6 carbon atoms, and a group including an aryl group and having from 6 to 12 carbon atoms;

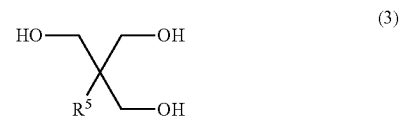

wherein $R^5$ denotes a hydrocarbon group;

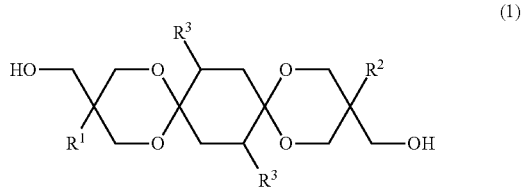

wherein $R^1$ and $R^2$ each independently denote a hydrocarbon group; and wherein $R^3$ each independently denotes at least one selected from the group consisting of a hydrogen atom, a heteroatom-containing group, a halogen atom-containing group, a linear alkyl group having from 1 to 6 carbon atoms, a branched alkyl group having from 3 to 6 carbon atoms, and a group including an aryl group and having from 6 to 12 carbon atoms.

2. The method for producing a diol according to claim 1, wherein $R^4$ in Formula (2) is each independently selected from the group consisting of a hydrogen atom, a linear alkyl group having from 1 to 6 carbon atoms, a branched alkyl group having from 3 to 6 carbon atoms, and a group including an aryl group and having from 6 to 12 carbon atoms.

3. The method for producing a diol according to claim 1, wherein $R^4$ in Formula (2) is each independently selected from the group consisting of a hydrogen atom and a methyl group.

4. The method for producing a diol according to claim 1, wherein $R^5$ in Formula (3) denotes at least one selected from the group consisting of a linear alkyl group having from 1 to 7 carbon atoms, a branched alkyl group having from 3 to 7 carbon atoms, and an aryl group.

5. The method for producing a diol according to claim 1, wherein $R^5$ in Formula (3) is a linear alkyl group having from 1 to 7 carbon atoms or an aryl group.

6. The method for producing a diol according to claim 1, wherein $R^4$ in Formula (2) is a hydrogen atom, and $R^5$ in Formula (3) is at least one selected from the group consisting of an ethyl group, a methyl group, and a phenyl group.

7. The method for producing a diol according to claim 1, wherein the cyclodehydration reaction is carried out at a temperature of 80° C. or less.

8. The method for producing a diol according to claims 1, wherein water is added as the solvent such that a theoretical yield of the diol represented by Formula (1), calculated from added amounts of the 1,4-cyclohexanedione derivative represented by Formula (2) and the triol represented by Formula (3), is 3 mass % or more of a total mass of the added amount of water as the solvent and the theoretical yield.

9. The method for producing a diol according to claim 1, wherein the cyclodehydration reaction is carried out with an acid catalyst.

10. The method for producing a diol according to claim 9, wherein the acid catalyst contains comprises at least one selected from the group consisting of a methanesulfonic acid and a para-toluenesulfonic acid.

11. The method for producing a diol according to claims 1, wherein the 1,4-cyclohexanedione derivative represented by Formula (2) is 1,4-cyclohexanedione, and wherein the triol represented by Formula (3) is at least one selected from the group consisting of trimethylolpropane, trimethylolethane, and tris(hydroxymethyl)toluene.

12. The method for producing a diol according to claims 1, further comprising filtering a reaction solution after the cyclodehydration reaction to produce a filtrate, adding to the filtrate a 1,4-cyclohexanedione derivative represented by Formula (2) and a triol represented by Formula (3) and carrying out a second cyclodehydration reaction.

* * * * *